US012685793B2

(12) United States Patent
Niedermann

(10) Patent No.: US 12,685,793 B2
(45) Date of Patent: Jul. 21, 2026

(54) DEVICE FOR SURFACE DISINFECTION OF THE INPUT FIELD OF CARD READERS FOR CREDIT CARDS, SUBSCRIPTIONS AND PAYMENT CARDS OF ALL KINDS

(71) Applicant: Yves Swiss AG, Sursee (CH)

(72) Inventor: Claude Niedermann, Oberkirch (CH)

(73) Assignee: Yves Swiss AG, Sursee (CH)

( * ) Notice: Subject to any disclaimer, the term of this patent is extended or adjusted under 35 U.S.C. 154(b) by 792 days.

(21) Appl. No.: 18/013,997

(22) PCT Filed: Apr. 23, 2021

(86) PCT No.: PCT/EP2021/060755
§ 371 (c)(1),
(2) Date: Dec. 30, 2022

(87) PCT Pub. No.: WO2021/244804
PCT Pub. Date: Dec. 9, 2021

(65) Prior Publication Data
US 2025/0186637 A1 Jun. 12, 2025

(30) Foreign Application Priority Data

Jun. 4, 2020 (CH) ..................................... 00666/20

(51) Int. Cl.
*A61L 2/10* (2026.01)
*A61L 2/24* (2006.01)
(52) U.S. Cl.
CPC .. *A61L 2/10* (2013.01); *A61L 2/24* (2013.01)
(58) Field of Classification Search
CPC .............................. A61L 2/10; A61L 2202/122
See application file for complete search history.

(56) References Cited

U.S. PATENT DOCUMENTS

| | | | | |
|---|---|---|---|---|
| 2008/0067417 | A1* | 3/2008 | Lane | A61L 2/24 |
| | | | | 250/455.11 |
| 2013/0098407 | A1* | 4/2013 | Perlman | A61B 90/70 |
| | | | | 49/260 |
| 2016/0010379 | A1* | 1/2016 | Sauerwein | E05F 5/00 |
| | | | | 49/350 |

FOREIGN PATENT DOCUMENTS

| | | | |
|---|---|---|---|
| DE | 202020002592 | U1 | 8/2020 |
| DE | 202020002907 | U1 | 10/2020 |

(Continued)

OTHER PUBLICATIONS

"Ultraviolet Disinfection: Crucial Link in the Sterilization Chain", https://www.terrauniversal.com/blog/ultraviolet-disinfection:-crucial-link-in-the-sterilization-chain/ (Downloaded from the Internet Apr. 17, 2023) 5 pages.

(Continued)

*Primary Examiner* — Kevin Joyner
*Assistant Examiner* — Changru Chen
(74) *Attorney, Agent, or Firm* — The Webb Law Firm

(57) ABSTRACT

The invention relates to a device for surface disinfection of card readers having an input field, a communication display and a receiving slot for credit cards, subscriptions and payment cards of all kinds to be inserted. The device includes a UVC lamp with which the entire input field of the card reader can be UVC-irradiated for disinfection. The device includes a movable housing with a UVC lamp incorporated therein for activating a disinfection cycle with direct irradiation of the input field of the card reader. For this purpose, the housing is brought into position over the input field.

6 Claims, 2 Drawing Sheets

(56) References Cited

FOREIGN PATENT DOCUMENTS

| WO | 2009147628 A1 | 12/2009 | |
| WO | WO-2019084203 A1 * | 5/2019 | ............ A61L 2/202 |

OTHER PUBLICATIONS

Wikipedia, "Germicidal Lamp", https://web.archive.org/web/20200510194253/https://en.wikipedia.org/wiki/Germicidal_lamp (Downloaded from the Internet Apr. 17, 2023) 4 pages.

* cited by examiner

DEVICE FOR SURFACE DISINFECTION OF THE INPUT FIELD OF CARD READERS FOR CREDIT CARDS, SUBSCRIPTIONS AND PAYMENT CARDS OF ALL KINDS

CROSS-REFERENCE TO RELATED APPLICATIONS

This application is the United States national phase of International Application No. PCT/EP2021/060755 filed Apr. 23, 2021, and claims priority to Swiss Patent Application No. 00666/20 filed Jun. 4, 2020, the disclosures of which are hereby incorporated by reference in their entirety.

BACKGROUND OF THE INVENTION

Field of the Invention

About half of all colds are caused by rhinoviruses. A study conducted in hotel rooms by the University of Virginia, USA, showed that the pathogens were still contagious on door handles, TV remotes and light switches, among other things, at least a day later. According to the British health authority NHS, rhinoviruses are even still infectious outside the body for up to seven days. According to a research group at the University Hospital of Geneva, a large accumulation of influenza A viruses on a banknote can remain active for up to 17 days. According to the Journal of Infectious Disease, the pathogens survive on smooth plastic surfaces for about 48 hours. The novel coronavirus 2019-nCov can even remain contagious outside the body for up to 9 days. Thus, a person can readily be infected via an object contaminated several days earlier by an infected person.

Description of Related Art

Ultraviolet C radiation (UVC) is the germicidal region of the ultraviolet spectrum with a wavelength in the range of 280 to 100 nm. UV Germicidal Irradiation (UVGI) has been studied for over a century. The effects of UVGI on common bacteria, viruses, and mold spores are well known. Since the mid-20th century, disinfection by UVGI has been accepted practice, primarily in medical hygiene and sterile work areas, and more recently it has been used to sterilize drinking water and wastewater or in air purifiers. Basically, applications of UVC irradiation fall into two categories: Surface disinfection and air stream disinfection. In surface disinfection, UVC radiation is applied to wall or chamber surfaces, as well as to surfaces of manufactured samples. As long as the surfaces to be disinfected are in the line of sight of the lamp, disinfection can be achieved within a few minutes by means of UVC exposure, depending on the dose. Whole room sanitizers offer this germicidal control for walls, ceilings and floors of laboratories, clean rooms or other production areas.

In the state of the art, UVC sanitizers are known for glove boxes, insulators and hoods. However, what significantly limits the applicability of germicidal UVC irradiation is the need for direct exposure. If the UVC source is too far away or moved out of the direct line of sight, or if the exposure time is too short, this is associated with reduced efficacy. Another issue relates to material degradation as a result of UVC exposure over a long period of time. Although UVC radiation is not harmful to most materials in a laboratory or cleanroom, including metals, painted surfaces and most plastics, elastomers and paper-based products age prematurely under the influence of UVC irradiation. Another issue is the harmfulness of UVC radiation to humans. The light can cause sunburn and over time even skin cancer on the skin at the appropriate intensity, and also lead to very painful inflammation of the eye cornea, up to permanent sea disorders. For this reason, UVC radiation produced by a germicidal lamp should be shielded so that it cannot directly strike human skin and a person cannot look directly into the UVC light. Source:

https://web.archive.org/web/20200510194253/https://en.wikipedia.org/wiki/Germicidal_lamp.

Accordingly, the everyday use of UVC lamps for disinfection is restricted.

Although small housing sizes allow effective UVC irradiation with lamps of lower power and shorter cycle times. In as little as about 30 seconds, surfaces of everyday objects can be rendered virtually germ-free from a UVC sanitizer. Because standard glass and many plastics, including acrylic, PVC and polycarbonate, effectively shield against UVC, UVC lamps can be safely integrated without endangering a nearby person (source:

https://web.archive.org/web/20200508142434/https://www.terrauniversal.com/blog/ultraviolet-disinfection:-crucial-link-in-the-sterilization-chain/.

However, for practical reasons, one will not carry such a UVC sanitizer on the go. The disinfection of objects to be touched, however, is particularly important when there is no immediate opportunity to wash and disinfect hands.

SUMMARY OF THE INVENTION

The most common situation that makes disinfection desirable is everyday card payments. The increasing proportion of card payments has also increased security requirements. Contactless payment is only possible up to a certain maximum amount per payment, as well as a maximum amount over several uses. Afterwards, a new PIN entry is required (according to Payment Services Directive (EU) 2015/2366). Thus, in everyday life, it is often not possible to avoid direct contact with a card reader. A fortiori, there is a great need for protection against disinfection for people who have the contactless function deactivated on their payment cards for security reasons, and therefore have to enter a PIN code manually for every single card payment. This applies analogously to other payment cards, such as parking cards, which require contact with the card reader. And with each direct contact, germs from the user remain on the input field of the card reader. Because the card readers are continuously operated and thus touched by many different people, they are veritable hotbeds of germs.

In view of the considerable need for disinfection in everyday life—as has recently become apparent as a result of the COVID-19 outbreak—the object of the present invention is to disclose a device for the surface disinfection of the input field of card readers for credit cards, subscriptions and payment cards of all kinds, which makes it possible to process card payments largely free of germs. The invention is intended to make such disinfection quick and easy and to be adaptable to any need.

The task is solved by a device for surface disinfection as described herein.

BRIEF DESCRIPTION OF THE DRAWINGS

With reference to the figures, the device and the method carried out with it are described and explained.

3

Figure 1:
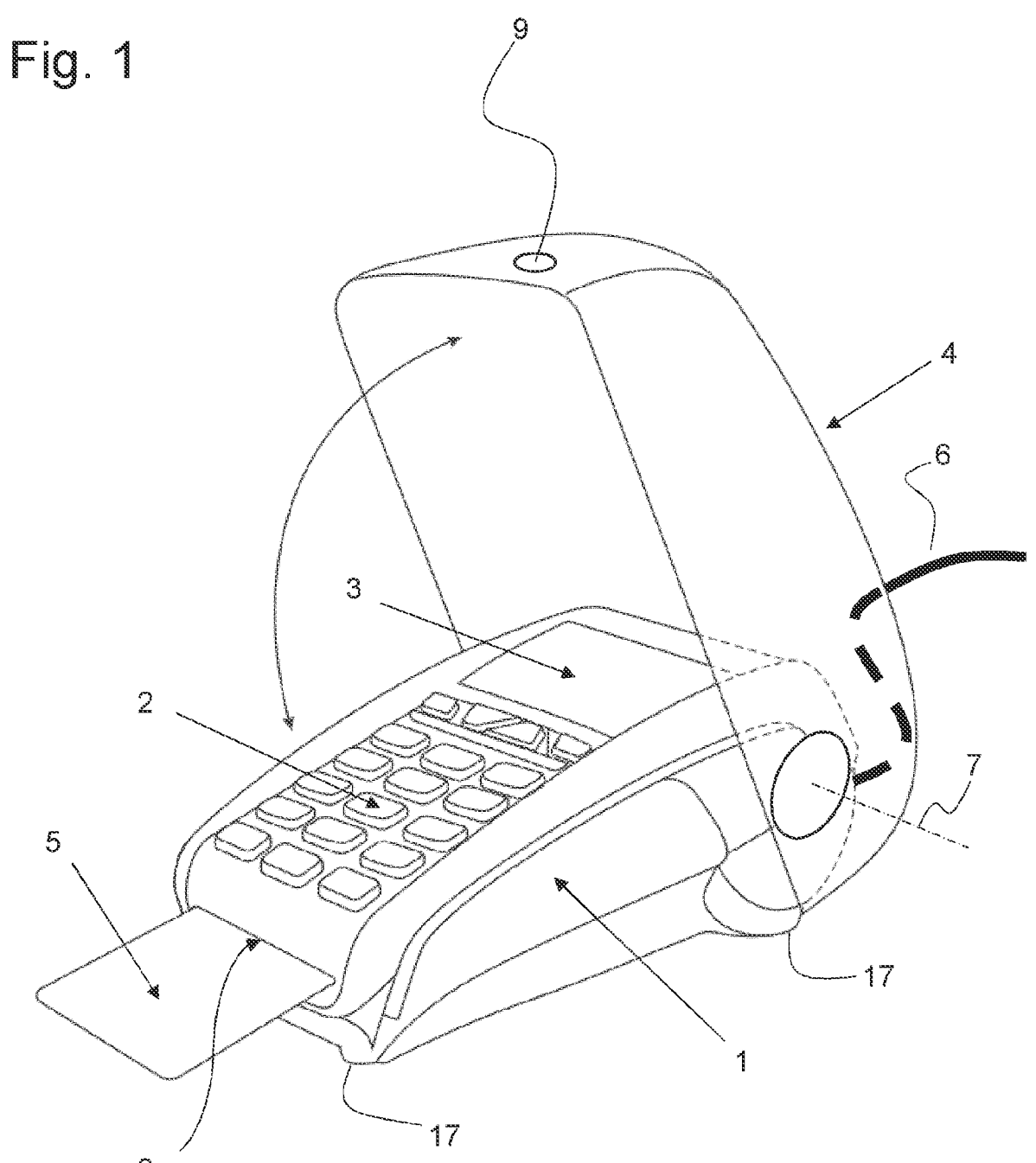

It shows:

FIG. 1: A device for surface disinfection of a mains-operated card reader in perspective view; and FIG. 2: An adapter for the surface disinfection of a battery-operated and thus mobile card reader in perspective view.

DESCRIPTION OF THE INVENTION

FIG. 1 shows a first embodiment of the device for surface disinfection of the keypad of a card reader 1 for credit cards 5, subscriptions or other payment cards, which operates by means of UVC irradiation of the keypad. The card reader has a display 3 and an input field 2 via which the user makes manual entries, such as a PIN entry or other manual authentication. This input field 2 can be a keypad, as in an ATM, or an input field 2 in the form of a touch screen, such as those that have been widely used in recent times. Due to its use by numerous persons or by an indeterminable group of persons, the input field 2 is a surface on which many germs naturally accumulate. In order to prevent their transmission from user to user, this device includes a germicidal lamp by means of which UVC light can be irradiated onto the input field 2 of the card reader 1 with such an intensity that it achieves a satisfactory degree of purity or a sufficiently high degree of disinfection for the respective purposes and needs. The duration of a UVC irradiation can be adjusted with advantage. This also allows flexible handling when card payments are carried out at high frequency. In this case, depending on the rush at the cash register, the standard setting time can be throttled or the disinfection function can even be switched off if necessary.

To ensure that the paying person is not harmed by the process of UVC exposure, the irradiation is consistently shielded, effectively preventing direct contact with human skin or the human eye. For this purpose, the area of the card reader 1 to be irradiated is shielded by a housing 4 before each UVC exposure. The irradiation then takes place in the all-around closed state of the keypad of the card reader 1. When the process of irradiation is completed, the housing 4 releases the keypad or input field 2 and the display 3. The housing 4 is arranged here to pivot about an axis 7 relative to the card reader 1, and an associated actuating device can pivot the housing 4 up to this open pivoted position shown, and down again if required. After the housing 4 has been swung down onto the card reader 1, the latter lies in such a way that the area to be irradiated is covered by the housing 4 and enclosed in such a way that direct contact of the skin and eyes of a user with the UVC radiation is prevented. In the embodiment shown in FIG. 1, the card reader 1 is enclosed by the closed housing 4. To secure the housing 4 in the swung closed condition, the housing 4 and the card reader 1 enclose an interlocking holding device, magnetic or otherwise, which ensures that the housing 4 cannot swing open during the irradiation process. Typically, such a detent includes a latch. Because the housing 4 is pivotally mounted, it will not fully enclose the card reader 1 when swung closed, leaving visible the lowermost portion or feet 17 on which the card reader 1 stands. Advantageously, the housing does not protrude over the slot 8 on the card reader 1 for inserting the card 5 when swiveled closed, but it can also cover the slot, depending on the design. In any case, the closed housing 4 encloses with the card reader 1 an interior space which is shielded and ready for UVC irradiation. Thus, temporarily, i.e. for the duration of the irradiation, access to the input field 2 is no longer possible. For the irradiation, a UVC lamp or a UVC radiator is arranged on the inside of the housing 4 in such a way that it can irradiate the input field of the card reader 1. The UVC lamp is either stationary, in which case the radiation field it generates covers the entire area to be irradiated, or it is movably mounted, and for this purpose moves over the area to be irradiated, for example along guide rails attached to the housing 4. Depending on this, this area can be covered once or several times. In a further embodiment, the UVC lamp is pivotably mounted, whereby the radiation field sweeps over the area to be irradiated by virtue of the pivoting movement. This pivoting movement can be performed once or several times.

The swiveling up and down of the housing 4 can be realized, for example, with a solenoid. In the basic state, the pivotable housing 4 is pivoted shut against the force of a pivot spring. Each time the housing 4 is swung shut, the housing 4 latches onto the unit in the swung-down position and the UVC radiation is immediately activated in this secured position. In an advantageous variant, each time the housing 4 is swung shut, an indicator light 9 on the housing 4 switches to red light. The card reader 1 is out of operation while the indicator light 9 is illuminated. Alternative control indicators may also be incorporated, such as a display indicating in the respective language or with understandable symbols that the device is being disinfected or is already available for use again. The housing 4 of the device may also swing open and closed purely by electric motor.

In another embodiment of the device, the housing 4 has a recess which, in its swung closed state, leaves the area of the receiving slot 8 free for the input of a card 5. If a credit card 5 is pushed into the receiving slot 8 in an embodiment of the device with control light 9, there are two possibilities: Either the irradiation is still in progress, which is indicated by a control light 9 in red, or the irradiation period has expired, which is indicated by the control light 9 in green. In the latter case, the housing 4 is immediately swung open by an internal electronic circuit and the input field 2 is exposed for use. As soon as the credit card 5 is pulled out of the slot 8 again, the control light changes to red and the device is deactivated for use by the internal electronic circuit. First, the housing 4 must be swung shut, which can be done either manually against the force of a spring on the hinge of the swivel axis 7 until it locks in the swung-down position, or by electric motor. The disinfection process is triggered by the engagement or snapping of the housing 4 on the card reader 1 via the electronic circuit. When the irradiation period has expired, for example after about 30 seconds, the housing 4 swings open, either by virtue of a spring on the hinge of the swivel axis 7, after which a pawl is retracted by, for example, a solenoid or a swivel lever, or by electric motor, in both cases triggered by the electronic circuitry inside. The control lamp 9 changes to green when the unit is swiveled open. The unit is ready to accept the next credit card 5, and especially to use the newly disinfected input field 2. Otherwise, when a card 5 is inserted into the slot 8 under the red light, the housing 4 remains swung shut until the irradiation period has expired. Thereafter, the housing 4 immediately swings upward to reveal the contact field. Each time a card 5 is pulled out of the receiving slot 8, the red indicator lamp 9 lights up to indicate that the keypad is unusable or does not respond to inputs. First, the housing 4 must be swung down, either manually or triggered by an electric motor. And as soon as it is swung down and locked in place, a new disinfection cycle begins while the indicator lamp 9 lights up red. This changes to green as soon as the disinfection cycle is completed. The housing 4 then remains swiveled shut until a next payment card 5 is inserted into the device, whereupon it opens immediately and releases the previously disinfected input field 2. As a result of the closed state of the housing 4, germs are prevented from accumulating again in the time period between the last use of the card reader 1 and the next use. The device is therefore always in a disinfected state, indicated by a green light, and does not need to be UVC-irradiated before being used again.

The swinging up and down of the housing 4 can be done by electric motor, which is particularly suitable for devices that are operated with a stationary power connection, for example card readers 1 in all kinds of sales stores. In this case, a small electric motor may be used, with the swinging up and down of the housing 4 being terminated by limit switches. In one possible embodiment, the electronic control reacts with an optical light barrier inside the slot 8, but an optical light barrier can also run outside the device, for example along or across the slot 8 and just in front of it. As soon as a card 5 is pulled out of the slot 8, the light barrier closes again and the housing 4 is subsequently swung shut. In a device with a control lamp 9, this switches to red and a disinfection cycle starts. As soon as the disinfection cycle is completed, the control lamp 9—controlled by the electronic built-in control unit-turns green and indicates that the card reader 1 is ready for use again. When a card 5 is inserted into the slot 8, the light barrier is interrupted and the housing 4 swings open to reveal the input field 2 for operation of the keys or touch screen. When an input has been made and the user is prompted on the display 3 to remove the card 5 and subsequently removes the card 5, the housing 4 swings down and closes the contact field. The control lamp 9 jumps back to red. A new disinfection cycle begins and when it is completed, the control lamp jumps from red to green. The initial state is reached.

The housing 4 can be opened by means of a spring force and closed manually against the same. This proves particularly useful for mobile card readers 1, such as those frequently used in the catering industry. In this case, it is also advantageous that the housing 4 has a recess which, when swung shut or closed, leaves the receiving slot 8 for a credit card 5 free. In the closed state, the housing 4 latches onto a holding device and is secured with a latch. However, a holding device can also be implemented magnetically or otherwise. A solenoid built into the bottom of the housing reacts to the insertion of a card 5. If no disinfection is in progress, which is indicated in green in an embodiment with a control lamp 9, in the mechanical embodiment with a latch the solenoid pulls back this latch and the housing 4 swings open about the axis 7 by virtue of the spring built into the hinge area. The entry can be made on the now released disinfected entry field 2 and after the card 5 has been pulled out, the person checking in swivels the housing 4 manually closed, against the acting spring force, until the housing 4 snaps back into place at the latch. A control lamp 9 immediately switches to red and a disinfection process starts. After the disinfection process has been completed, the indicator lamp 9 switches to green and the card reader 1 is ready for the next insertion of a payment card 5. As soon as one is inserted, the housing 4 pops open to reveal the disinfected input field 2.

Figure 2:
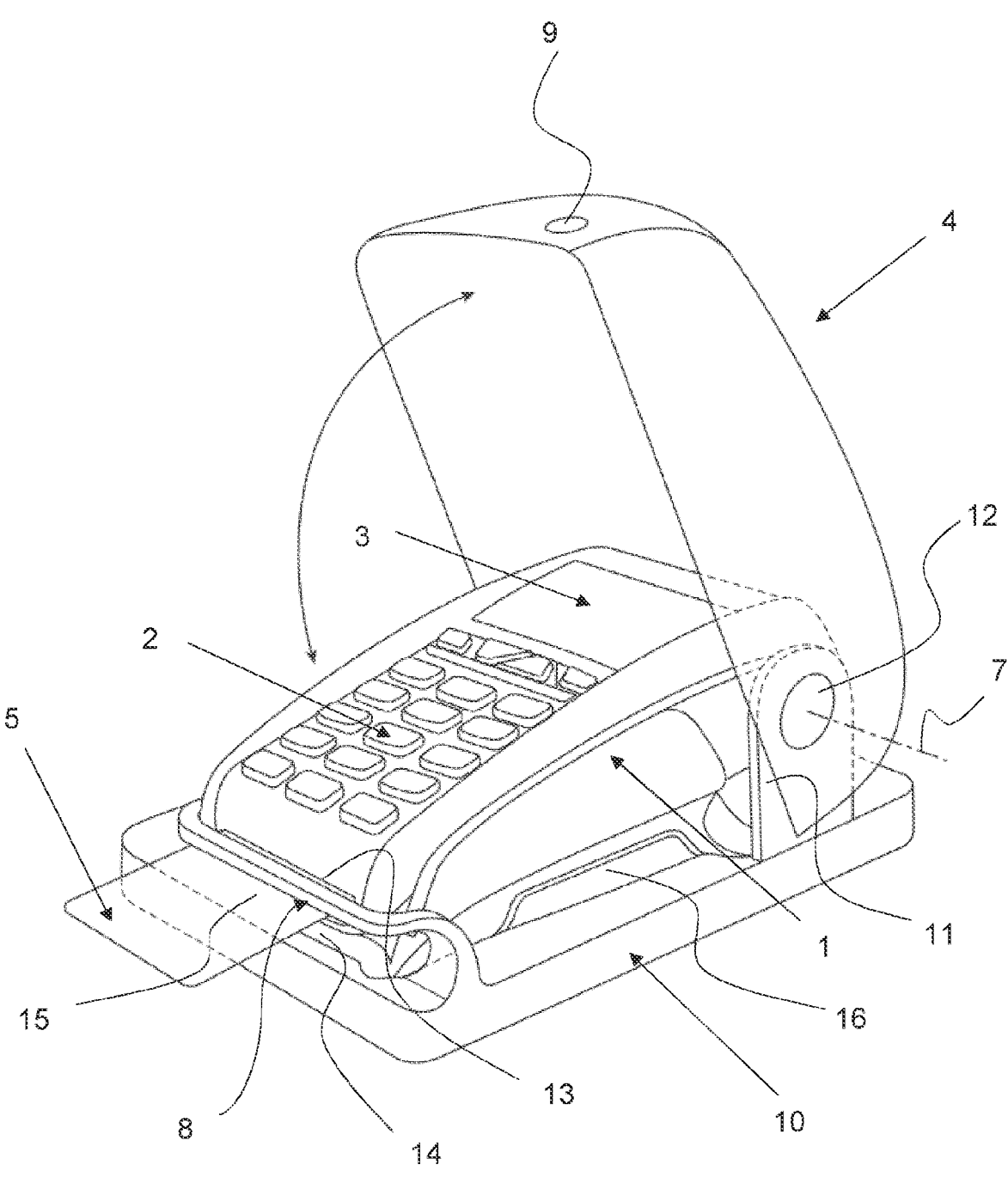

This device can also be designed as an adapter for retrofitting existing card readers 1. Such a retrofit unit is shown in FIG. 2. In contrast to the design according to FIG. 1, the housing 4 is not hinged to the card reader 1, but is pivotably mounted on a separate pedestal 10 belonging to the adapter. The pedestal 10 has a lip 13 at the front which runs along and above the receiving slot 8. Another lip 14, which is covered by the card 5 in FIG. 2, contains a light emitter for a light barrier 15. This light barrier 15 closes when the card 5 is removed, causing the housing 4 to swing shut and the disinfection to be activated after the closed position has been assumed. Whereas in the case of an integral device as shown in FIG. 1 the card reader 1 can be switched in such a way that it controls the swivelling movements of the housing 4 itself, in the variant of the adapter this function must be ensured by the adapter itself, for example by virtue of the information from the light barrier 15 triggering a current pulse on a solenoid or a swivelling lever which releases the housing 4 from its latched position secured by a latch. The housing 4 remains in this closed position until the next use. A card 5 is then inserted into the receiving slot 8 under this lip 13. The mass of the pedestal 10, of the lips 13 and 14, of the two lateral wings 16 and of the axis holder 11 of the pedestal 10 are such that a conventional card reader 1 can be embedded therein with an accurate fit. Preferably, the lateral wings 16 are adjustable in their mutual distance, so that one and the same adapter can be used for card readers 1 of different widths, the position of which is secured by adjusting the distance of the wings 16. Optionally, the lateral wings 16 are made of a slightly yielding material, so that they protrude slightly inwardly without a card reader 1 and, when such a card reader is embedded, clamp it snugly or engage therein. Similarly, the lip 13 with light sensor and the lip 14 with light emitter for the light barrier 15 can also be of adjustable length so that they can be adapted to card readers 1 of different lengths.

However, the device does not require an almost entirely shielding housing 4 as shown in FIGS. 1 and 2. The UVC lamp may also be attached to a movably mounted housing, the sole function of which is to ensure the positioning of the UVC lamp for the process of irradiation. For this purpose, when a disinfection cycle is activated, the housing moves from the initial position to such a position that the UVC lamp is directed towards the contact field to be irradiated. For this purpose, the housing can be pivoted open and closed, retracted and extended, or otherwise moved. While the UVC lamp is moved by the housing into position for irradiation or away from that position, the irradiation process is disabled, effectively preventing direct contact of the user of the device with the UVC radiation. If the housing does not shield the irradiation area to such an extent that it is impossible to reach into this irradiation area during UVC irradiation, the device is equipped with a sensor that deactivates UVC irradiation as soon as an object or a finger moves over the critical area and as soon as the device is no longer horizontal on the floor. The variant with the almost completely shielding housing is advisable wherever the device is exposed at an elevated position, such as at a checkout counter, in such a way that a child could look into the actively irradiating UVC lamp from below. In the case of an almost completely or hermetically sealed housing 4, this is not possible.

The device may have a power connection 6 and/or be battery powered. In this regard, the device can communicate with a central system unit via the cable 6 or else wirelessly, via which changes in the settings can be made, such as a shorter or longer irradiation interval. Alternatively, such settings can also be made directly on an individual device, for example via a smartphone app. Where possible, sensors are connected to the device and/or to the central system unit that detects a number of people waiting. Alternatively, the frequency of card payments is recorded. Depending on the rush or frequency of use, the duration of the irradiation intervals is adjusted, i.e. if there is a large rush and frequency, the irradiation interval is shorter or the UVC irradiation is switched off completely, for example if a large queue is still formed in front of a checkout shortly before closing time. Preferably, the device has an abort button that allows a user to stop the irradiation process immediately, for example if he is pressed for time and cannot wait until the end of a disinfection process that has not yet been completed before making his payment. Such also proves to be convenient if a wrong card 5 is accidentally inserted into the card reader 1 and immediately removed. The disinfection cycle triggered by the removal of the wrong card 5 can then be immediately terminated by means of the cancel button, allowing the user to make the payment immediately with the correct card 5. The card reader 1 also does not necessarily need to stop its functionality during the irradiation process.

LIST OF NUMERALS

1 Card reader
2 Contact field, keypad
3 Display
4 Housing, hinged
5 Credit card
6 Power cable
7 Swivel axis of housing 4
8 Slot on card reader 1, for inserting a card 5
9 Control lamp
10 Pedestal of the adapter
11 Axis holder
12 Axis bolt, molded onto housing 4
13 Lip above slot 8
14 Lip below slot 8, with light transmitter for light barrier
15 Light barrier
16 Lateral wings as holder
17 Feet of card holder 1

The invention claimed is:

1. A device for the surface disinfection of card readers with system comprising:

a card reader having an input field, a communication display and a receiving slot for credit cards, subscriptions and payment cards of all kinds to be inserted; and a device for the surface disinfection of the card reader, the device comprising a UVC lamp by which an entire input field of the card reader is directly irradiatable for disinfection; and a movable housing with the UVC lamp installed therein, wherein the housing is designed as a hollow cover, in an interior of which the UVC lamp is installed, for direct irradiation of the input field of the card reader, wherein the housing is pivotably mounted on a housing of the card reader and is biased by a spring toward an open position in which the input field is released, and can be pivoted manually against the spring force into closed position in which the housing covers the input field and is latched or snapped on the card reader or otherwise held in the closed position, wherein the device further comprises an electronic circuit and a control light provided on the housing, the electronic circuit being configured such that:

when the housing is in the closed position, the control light lights up red and a disinfection cycle with operation of the UVC lamp is started;

after completion of the disinfection cycle and only after such completion, when a card is inserted into the receiving slot of the card reader, the electronic circuit unlocks the latched, snapped-in or otherwise held housing so that the spring automatically pivots the housing into the open position, the control light changes to green, and the input field is released for operation by a user; and when the card is pulled out of the receiving slot of the card reader, the electronic circuit switches the control light back to red, deactivates the input field and allows the housing to be pivoted manually against the spring force back into the closed position in which a new disinfection cycle is started, and after completion of the new disinfection cycle the electronic circuit switches the control light again to green.

2. The system according to claim 1, wherein the housing is designed as the hollow cover pivotably mounted on the card reader and is additionally swingable by an electric motor, and wherein the device further comprises the electronic circuit of claim 1 configured such that:

when the housing is in the closed position or swung down, the control light lights up red and a disinfection cycle begins;

after a disinfection cycle has been completed and the control lamp has changed to green, when a card is inserted into the card reader, the electronic circuit drives the electric motor to swing open the housing into the open position and releases the input field;

when the card is pulled out of the card reader, the electronic circuit switches the control light to red, makes the input field inactive and drives the electric motor to swing down the housing into the closed position, in which the electronic circuit starts a new disinfection cycle; and the electric motor is controlled by limit switches that stop the electric motor in defined end positions of the housing.

3. The system according to claim 1, wherein the device is designed as an adapter, for retrofitting an existing card reader, the device comprising a pedestal with a rechargeable battery and the electronic circuit, and wherein the card reader can be placed on the pedestal in a snap-in or firmly adhering manner.

4. The system according to claim 3, wherein a part of the pedestal in front of the receiving slot of the attached card reader forms an upper lip and a lower lip between which a card can be inserted into the card reader, wherein the upper and lower lips are traversed by a light barrier belonging to the adapter, and wherein, when the light barrier is interrupted by the card, the housing, which can be swiveled shut manually against the spring force or by means of the electric motor, is held in the closed position during a disinfection cycle and, after completion of the disinfection cycle and insertion of a new card, the housing is swung open by the electric motor or by force of the previously tensioned spring to release the input field for payment with the new card.

5. The system according to claim 1, wherein a number of persons waiting in front of the card reader and/or a frequency of card payments made is detected at a central system unit to which the device is connected, and wherein a duration of irradiation intervals of the disinfection cycle is adjustable depending on the detected number of persons and/or the payment frequency.

6. The system according to claim 1, wherein changes in settings of the device can be entered via a cable, wirelessly via a central system unit, or directly on the device itself.

\* \* \* \* \*